Dec. 3, 1957 G. J. VON ABRAMS Plant Pat. 1,662
ROSE PLANT
Filed Feb. 25, 1957
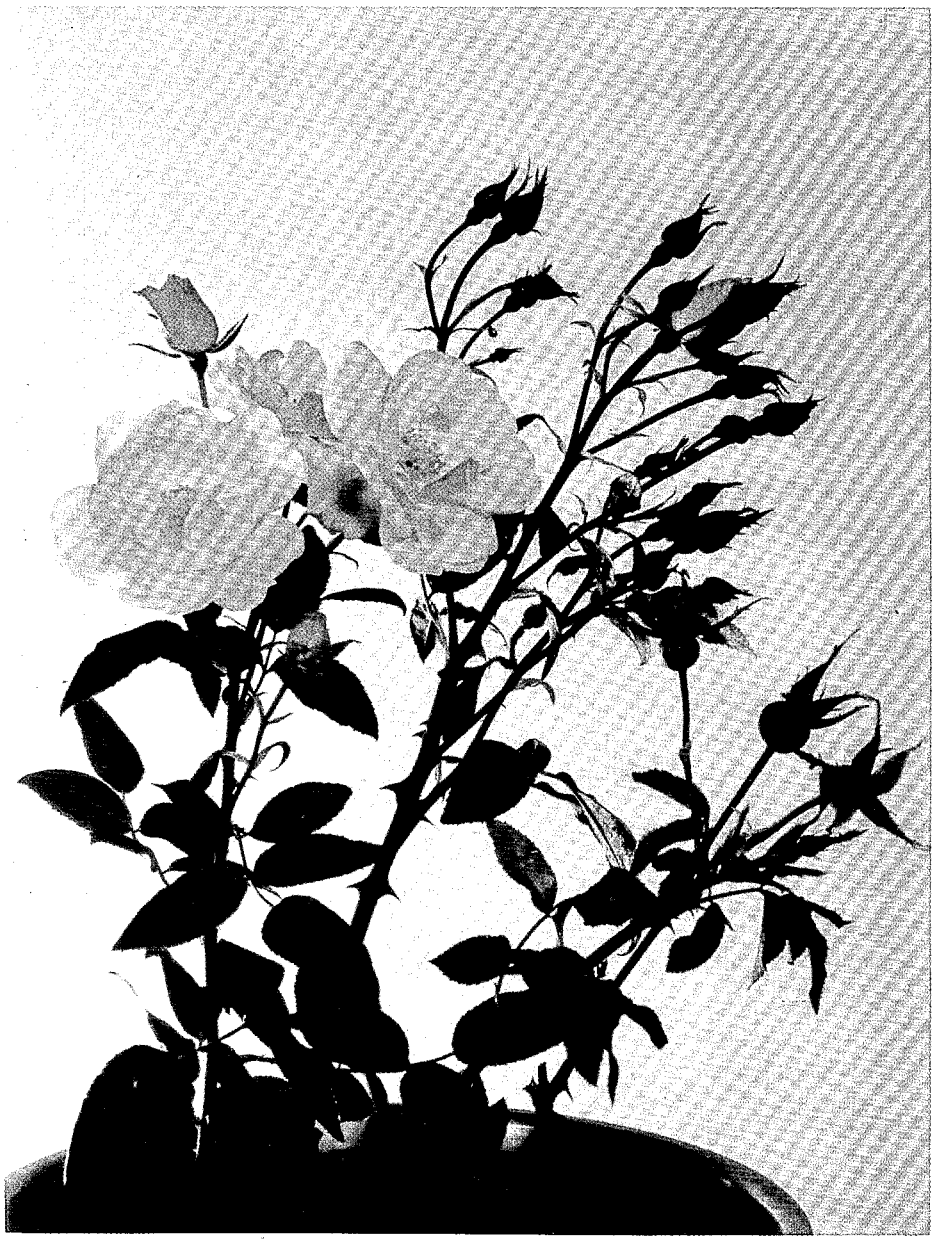
INVENTOR
G. J. Von Abrams
BY Robert Cobb
ATTORNEYS United States Patent Office Plant Pat. 1,662
Patented Dec. 3, 1957

1,662

ROSE PLANT

Gordon J. Von Abrams, Scappoose, Oreg., assignor to Eldon Pinkeney Dering, doing business under the trade name of Peterson & Dering, Scappoose, Oreg.

Application February 25, 1957, Serial No. 642,325

1 Claim. (Cl. 47—61)

The present invention relates to a new and distinct variety of rose plant of the floribunda class, which was originated by me by crossing the variety "Else Poulsen" (unpatented) with the variety "Captain Thomas" (Plant Patent No. 393).

The primary objective of this breeding was to produce a new rose variety of the floribunda class and of the "Else Poulsen" type, but which has heavier, glossy foilage, greater disease resistance, greater vigor and larger flowers of a more yellow color and with less blue pigment. This objective was fully achieved, as evidenced by the following phenotypic characteristics which are particularly outstanding in the new variety:

(1) The upright, bushy and vigorous habits of growth of the plant which attains an average medium height of approximately 3 feet;

(2) The medium-dark, glossy foliage which is well-distributed;

(3) The above-average disease resistance;

(4) The continuous flowering habit and very prolific production of the flowers which are borne in large clusters; and (5) The unique combination of form and color of the flowers, as hereinafter more specifically described, and which is distinct from all other varieties of which I am aware.

In comparison with its seed parent, "Else Poulsen," my new variety has longer leaves which are more narrow and darker in color, with stipules broader and more bristly than the foliage of this parent; its prickles and thorns are less numerous; its disease resistance is much improved, particularly with respect to mildew; and the flowers have much less blue pigmentation, are larger, have more petals and better form, and have a brighter general appearance.

As compared with its pollen parent, "Captain Thomas," my new variety has a dwarf habit of growth, as distinguished from a climbing habit; the leaves are smaller, darker, less glossy and more nearly lanceolate than those of this parent; and the flowers have more petals and are not as yellow in color.

Asexual reproduction of the new variety by bud-grafting, as performed by me at Scappoose, Oregon, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated as "Wilson") and Robert Ridgway's Color Standards and Nomenclature (hereinafter abbreviated as "Ridgway"), except where general color terms of ordinary dictionary significance are obvious:

Type: Hardy; bush; outdoor; seedling; for garden decoration.

Class: Floribunda.

Parentage: Seedling.

*Seed parent.*—"Else Poulsen."

*Pollen parent.*—"Captain Thomas."

Propagation: Holds its distinguishing characteristics through succeeding propagations by bud-grafting.

*Flower*

Locality where grown and observed: Scappoose, Oregon.

Flowers borne: In irregular, large rounded clusters; on normally short stems of approximately 6 cm. in length.

Quantity of bloom: Abundant.

Continuity: Continuous during growing season outdoors.

Fragrance: Moderate. Nature—spicy.

Bud:

*Peduncle.*—Short; from about 3 to 6 cm. in length; moderately heavy; medium stiff; with numerous glandular cilia. Color—Light Green, with early Red flush.

*Before calyx breaks.*—Size—small; about 1 x 2 cm., excluding receptacle. Form—pointed; with conspicuous neck; without foliaceous appendages on the surface of the bud, but with two and sometimes more, appendages on the lateral margins of alternate sepals; with serrate foliaceous parts extending beyond the tip of the bud usually less than ¼, but sometimes more than ½, the length of the bud; with the outer surface of the sepal moderately rough and often glandular. Color—Near Scheele's Green, Plate 860/2, page 175 (Wilson), later flushed with Maroon.

*As calyx breaks.*—Color—Near Spinel Red, Plate XXVI, 71′, V-RR (Ridgway).

*As first petal opens.*—Size—small; about 16 x 28 mm. Form—medium pointed. Color: outside—Cherry, Plate 722/3, page 157 (Wilson), flushed with Gold at base; inside—Near Lemon Chrome, Plate IV, 21 (Ridgway) at base, flushed upward from Shrimp Pink, Plate I, 5 (Ridgway) to La France Pink, Plate I, 3 (Ridgway) at apex.

*Opening.*—Opens up very well in all weather.

Bloom:

*Size.*—Small; about 6.5 to 9.0 cm.

*Petalage.*—Semi-double; from 10 to 14 petals; arranged regularly.

*Form.*—Cupped at first, but becoming open; petals remain lightly rolled inward well into maturity.

Petals:

*Texture.* — Medium thick; soft. Inside — satiny. Outside—satiny.

*Shape.*—Outside—obovate; about 3.5 x 3.8 cm. Inside—narrow obovate; about 2.5 x 3.3 cm.; apex usually emarginate.

This description of a newly opened flower was made from a rose grown outdoors in the month of August, at Scappoose, Oregon:

*Color.*—Outer petal: outer surface—Deep Rose Pink, Plate XII, 71, *d* (Ridgway), flushed with Rose Color, Plate XII, 7, *b* (Ridgway), with basal flush of Chalcedony Yellow, Plate XVII, 25′, *b* (Ridgway); inner surface—Near Cameo Pink, Plate XXVI, 71′ *f* (Ridgway), flushed upward from base with Picric Yellow, Plate IV, 23, *b* (Ridgway). Inner petal: outer surface—from Deep Rose Pink, Plate XII, 71, *d* (Ridgway), to Rose Pink, Plate XII, 71, *f* (Ridgway), with basal flush of Chalcedony Yellow, Plate XVII, 25′, *b* (Ridgway); inner surface—from Camellia Rose, Plate 622/3, page 148 (Wilson) to Camellia Rose, Plate 622/2, page 148 (Wilson), flushed upward from base with Picric Yellow, Plate IV, 23, *b* (Ridgway).

This description was made from a rose which was open for three days outdoors in the month of August, at Scappoose, Oregon:

*Color.*—Outer petal: outer surface—Rose Pink, Plate XII, 71, *f* (Ridgway), with base Near White; inner surface—Near White, washed from apex with Rose Pink, Plate XII, 71, *f* (Ridgway). Inner petal: outer surface—Rose Pink, Plate XII, 71, *f* (Ridgway), with base Near White; inner surface—Near White, washed from apex with Rose Pink, Plate XII, 71, *f* (Ridgway).

*General color effect.*—Near Thulite Pink, Plate XXVI 71′, *d* (Ridgway).

*Behavior.*—Petals drop off cleanly; fade gradually lighter to Near White on inner surface; show Tan spots in high temperature and sunlight.

*Flower longevity.*—On plant—4 days in August. Cut flowers grown outdoors and kept at room temperatures—2 days in August.

*Reproductive organs*

Stamens: Moderately numerous; arranged regularly about pistils on margin of receptacle.

Filaments: Short; usually less than 1 cm.; all with anthers. Color—Yellow.

Anthers: Small; open nearly at same time. Color—Orange.

Pollen: Abundant. Color—Dark Gold.

Pistils: About 40 in number.

Styles: Quite even; approximately 8 mm. long; thin; loosely bunched.

Stigma: Color—From Yellow-Green to Near White.

Ovaries: All enclosed in receptacle.

Hips: Small; about 1.5 x 1.7 cm.; from globular to slightly obovate; smooth; walls moderately thick and fleshy. Color (at maturity)—from Orange to Deep Red, depending upon environment.

Sepals: Persistent; upright; stiff; sometimes very long; up to 4 cm. long; with large serate terminal foliaceous appendages. Color—often near Scheele's Green, Plate 860, p. 175 (Wilson), but varying with environment.

Seeds: Many; medium size.

*Plant*

Foliage:

*Leaves.*—Odd-pinnate; usually 7 leaflets; abundant; medium large; medium heavy; leathery; glossy.

*Leaflets.*—Shape—ovate. Margin—simply serrate. Size—up to 7 x 4 cm.

*Color.*—Mature: upper surface—Near Dark Dull Yellow-Green, Plate XXXII, 31″, *m* (Ridgway), under surface—Near Chrome Green, Plate XXXII, 31″, *i* (Ridgway). Young: upper surface—Near Forest Green, Plate XVII, 29′, *m* (Ridgway); under surface—Near Light Elm Green, Plate XVII, 27′, *k*, (Ridgway), variably flushed with Maroon.

*Rachis (the supporting stem of the compound leaf).*—Heavy. Upper surface—grooved; with several glandular cilia on margins. Under surface—few thorns; with several glandular cilia.

*Stipules.*—Medium size; about 2 x 0.8 cm.; with medium points turning out at usually less than 45°; margins deeply serrate and nearly bristly.

Disease resistance: Better than average resistance to mildew and rust, as determined from comparison with other varieties grown under comparable cultural conditions at Scappoose, Oregon.

Growth:

*Habit.*—Upright; bushy; well-branched.

*Growth.*—Free.

*Canes.*—Medium caliper.

*Main stems.*—Color—Near Light Elm Green, Plate XVII, 27′, *k*, (Ridgway), where corky. Thorns—several; medium length; up to 1.3 cm. long; slightly hooked downward; with small obovate base about 9 x 3 mm. in size; color—Light Brown. Prickles—none. Hairs—none.

*Branches.*—Color—Near Bice Green, Plate XVII, 29′, *k* (Ridgway). Thorns—several; medium length; up to 1.3 cm. long; slightly hooked downward; with small obovate base about 9 x 3 mm. in size; color—Near Bordeaux, Plate XII, 71, *k* (Ridgway). Prickles — few; color—Reddish. Hairs—none.

*New shoots.*—Color — Variable Reddish color. Thorns—several; medium length; up to 1.3 cm. long; slightly hooked downward; with small obovate base about 9 x 3 mm. in size. Prickles—few; color—Reddish. Hairs—none, except on very small growth where there are a few glandular cilia.

I claim:

A new and distinct variety of rose plant of the floribunda class and of the "Else Poulsen" (unpatented) type, substantially as herein shown and described, characterized particularly as to novelty by the upright, bushy, vigorous, and medium tall habits of growth of its plant, its medium dark, glossy foliage and the good distribution thereof, its above-average disease resistance, its continuous and very prolific flowering habit throughout the growing season, with the flowers borne in large clusters, and the distinctive and unique combination of form and color of its flowers.

No references cited.